US00PP21267P2

(12) United States Plant Patent
Volmary

(10) Patent No.: US PP21,267 P2
(45) Date of Patent: Aug. 31, 2010

(54) ***BRACHYCOME* PLANT NAMED 'NEBBRA 001'**

(50) Latin Name: *Brachycome angustifolia*
Varietal Denomination: Nebbra 001

(75) Inventor: Hubertus Volmary, Everswinkel (DE)

(73) Assignee: Outback Plants Pty. Ltd., Cranbourne, Victoria (AU)

( * ) Notice: Subject to any disclaimer, the term of this patent is extended or adjusted under 35 U.S.C. 154(b) by 67 days.

(21) Appl. No.: 12/315,162

(22) Filed: Nov. 28, 2008

(51) Int. Cl.
*A01H 5/00* (2006.01)

(52) U.S. Cl. ..... Plt./411

(58) Field of Classification Search ..... Plt./411
See application file for complete search history.

*Primary Examiner*—Wendy C. Haas
(74) *Attorney, Agent, or Firm*—C. A. Whealy

(57) ABSTRACT

A new and distinct cultivar of *Brachycome* plant named 'Nebbra 001', characterized by its compact and mounding plant habit; freely branching growth habit; freely flowering habit; large inflorescences positioned just above the foliage; dark purple-colored ray florets; and good postproduction longevity.

2 Drawing Sheets

Botanical designation: *Brachycome angustifolia.*
Cultivar denomination: 'Nebbra 001'.

BACKGROUND OF THE INVENTION

The present invention relates to a new and distinct cultivar of *Brachycome* plant, botanically known as *Brachycome angustifolia* and hereinafter referred to by the name 'Nebbra 001'.

The new *Brachycome* plant is a naturally-occurring branch mutation of *Brachycome angustifolia* 'Billabong Mauve Delight', disclosed in U.S. Plant Pat. No. 10,899. The new *Brachycome* was discovered and selected by the Inventor on a single plant from within a population of plants of 'Billabong Mauve Delight' in a controlled greenhouse environment in Munster, Westfallen, Germany.

Asexual reproduction of the new *Brachycome* by vegetative cuttings in a controlled environment in Munster, Westfallen, Germany has shown that the unique features of this new *Brachycome* are stable and reproduced true to type in successive generations.

SUMMARY OF THE INVENTION

Plants of the new *Brachycome* have not been observed under all. possible environmental conditions. The phenotype may vary somewhat with variations in environment and cultural practices such as temperature and light intensity without, however, any variance in genotype.

The following traits have been repeatedly observed and are determined to be the unique characteristics of 'Nebbra 001'. These characteristics in combination distinguish 'Nebbra 001' as a new and distinct cultivar of *Brachycome:*

1. Compact and mounding plant habit.
2. Freely branching growth habit.
3. Freely flowering habit.
4. Large inflorescences positioned just above the foliage.
5. Dark purple-colored ray florets.
6. Good postproduction longevity.

Plants of the new *Brachycome* differ primarily from the mutation parent, 'Billabong Mauve Delight', in flower color as plants of the new *Brachycome* have darker purple-colored ray florets than plants of 'Billabong Mauve Delight'.

Plants of the new *Brachycome* can also be compared to plants of the *Brachycome angustifolia* 'Enduring Blue', disclosed in U.S. Plant Pat. No. 20,582. In side-by-side comparisons conducted in Cranbourne, Victoria, Australia, plants of the new *Brachycome* differed from plants of 'Enduring Blue' in the following characteristics:

1. Plants of the new *Brachycome* were more compact than plants of 'Enduring Blue'.
2. Plants of the new *Brachycome* had slightly thinner stems than plants of 'Enduring Blue'.
3. Plants of the new *Brachycome* had smaller leaves and inflorescences than plants of 'Enduring Blue'.
4. Plants of the new *Brachycome* and 'Enduring Blue' differed in ray floret color as plants of 'Enduring Blue' had lighter-colored ray florets.

BRIEF DESCRIPTION OF THE PHOTOGRAPHS

The accompanying colored photographs illustrate the overall appearance of the new *Brachycome*, showing the colors as true as it is reasonably possible to obtain in colored reproductions of this type. Colors in the photographs may differ slightly from the color values cited in the detailed botanical description which accurately describe the colors of the new *Brachycome.*

The photograph on the first sheet comprises a side perspective view of a typical flowering plant of 'Nebbra 001' grown in a container.

The photograph on the second sheet comprises close-up views of a typical flowering stem of 'Nebbra 001' (left) and a typical flowering stem of 'Billabong Mauve Delight' (right).

DETAILED BOTANICAL DESCRIPTION

The aforementioned photographs and following observations, measurements and values describe plants grown in containers in Cranbourne, Victoria, Australia, under commercial practice during the fall and winter in a polyethylene-covered greenhouse with day temperatures ranging from 8° C. to 30° C., night temperatures ranging from 2° C. to 22° C. and light levels ranging from 1,000 lux to 9,000 lux. Plants were pinched about four to six weeks after planting. Plants had been growing for three months when the photographs and description were taken. In the following description, color references are made to The Royal Horticultural Society Colour Chart, 1995 Edition, except where general terms of ordinary dictionary significance are used.

Botanical classification: *Brachycome angustifolia* 'Nebbra 001'.

Parentage: Naturally-occurring branch mutation of *Brachycome angustifolia* 'Billabong Mauve Delight', disclosed in U.S. Plant Pat. No. 10,899.

Propagation:

*Type.*—By vegetative cuttings.

*Time to initiate roots, summer.*—About 10 to 20 days at temperatures of 25° C.

*Time to initiate roots, winter.*—About 15 to 30 days at temperatures of 20° C.

*Root description.*—Thin, slightly fleshy; white in color.

*Rooting habit.*—Freely branching; moderately dense.

Plant description:

*Plant form/habit.*—Compact and mounded plant habit; moderately vigorous growth habit. Freely branching habit with numerous lateral branches developing after pinching.

*Plant height.*—About 10 cm to 20 cm.

*Plant width (spread).*—About 30 cm to 60 cm.

*Lateral branches.*—Length: About 2 cm to 6.5 cm. Diameter: About 1 mm. Internode length: About 5 mm to 15 mm. Strength: Moderately strong. Texture: Smooth, glabrous. Color: Close to 137D.

Foliage description:

*Arrangement.*—Alternate, simple; sessile.

*Length.*—About 1 cm to 4 cm.

*Width.*—About 5 mm to 15 mm.

*Shape.*—Oblong to spatulate.

*Apex.*—Acute to somewhat obtuse.

*Base.*—Attenuate.

*Margin.*—Three to five-lobed.

*Texture, upper and lower surfaces.*—Smooth, glabrous.

*Venation pattern.*—Pinnate.

*Color.*—Developing leaves, upper surface: Close to 137A. Developing leaves, lower surface: Close to 137C. Fully expanded leaves, upper and lower surfaces: Close to 137B; venation, close to 137B.

Inflorescence description:

*Appearance.*—Single composite inflorescence form with ray and disc florets. Inflorescences borne just above the foliage. Freely flowering habit with numerous inflorescences developing per plant during the flowering period.

*Fragrance.*—Not detected.

*Flowering season.*—Plants flower from spring through autumn in Australia; flowering continuous during this period. Plants begin flowering about four to eight weeks after planting.

*Inflorescence longevity.*—Inflorescences last about two to three weeks on the plant; inflorescences not persistent.

*Inflorescence bud.*—Height: About 1 mm to 2 mm. Diameter: About 2 mm to 3 mm. Shape: Oblate. Color: Between 138B and 143B.

*Inflorescence size.*—Diameter: About 1.5 cm to 2 cm. Diameter of disc: About 4 mm to 8 mm.

*Ray florets.*—Quantity/arrangement: About 16 to 25 in about two whorls. Shape: Lanceolate, narrowly oblong. Apex: Obcordate or retuse. Base: Attenuate. Margin: Entire. Length: About 6 mm to 10 mm. Width: About 1.5 mm to 2 mm. Texture, upper and lower surfaces: Smooth, glabrous. Color: When opening, upper surface: Between 82A and 87A. When opening, lower surface: Close to 87A. Fully opened, upper surface: Close to 87A; color becoming closer to 82A with development. Fully opened, lower surface: Close to 89D.

*Disc florets.*—Arrangement: Massed at center of receptacle. Shape: Tubular, elongated. Apex: Five-pointed. Length: About 3 mm. Width: About 1 mm. Texture: Smooth, glabrous. Color, immature: Close to 144A. Color, mature: Close to 12A.

*Involucral bracts.*—Quantity/arrangement: About 14 to 18 arranged in one to two whorls; bracts imbricate. Length: About 2 mm to 3 mm. Width: About 1 mm. Shape: Oblong. Apex: Acute to obtuse. Margin: Entire, fringed. Texture, upper and lower surfaces: Smooth, glabrous. Color, upper and lower surfaces: Close to 138B.

*Peduncles.*—Length, terminal peduncle: About 4.2 cm to 5.5 cm. Diameter: About 2 mm. Strength: Moderately strong. Texture: Smooth, glabrous. Color: Close to 138B.

*Reproductive organs.*—Present on disc florets only. Androecium: Filament length: Less than 1 mm. Filament color: Close to 155D. Anther length: Less than 1 mm. Anther shape: Oblong to lanceolate. Pollen amount: Moderate. Gynoecium: Stigma shape: Bilobed. Style length: About 3 mm. Style color: Close to 155D.

*Seeds.*—Seed set is nil to scarce on plants of the new *Brachycome*. Quantity per inflorescence: None to about three. Length: Less than 1 mm. Diameter: Less than 1 mm.

Disease/pest resistance: Plants of the new *Brachycome* have not been observed to be resistant to pathogens and pests common to *Brachycomes*.

Garden performance: Plants of the new *Brachycome* have been observed to have good garden performance and tolerate rain, wind and temperatures ranging from about −3° C. to about 44° C.

It is claimed:

1. A new and distinct B*rachycome* plant named 'Nebbra 001' as illustrated and described.

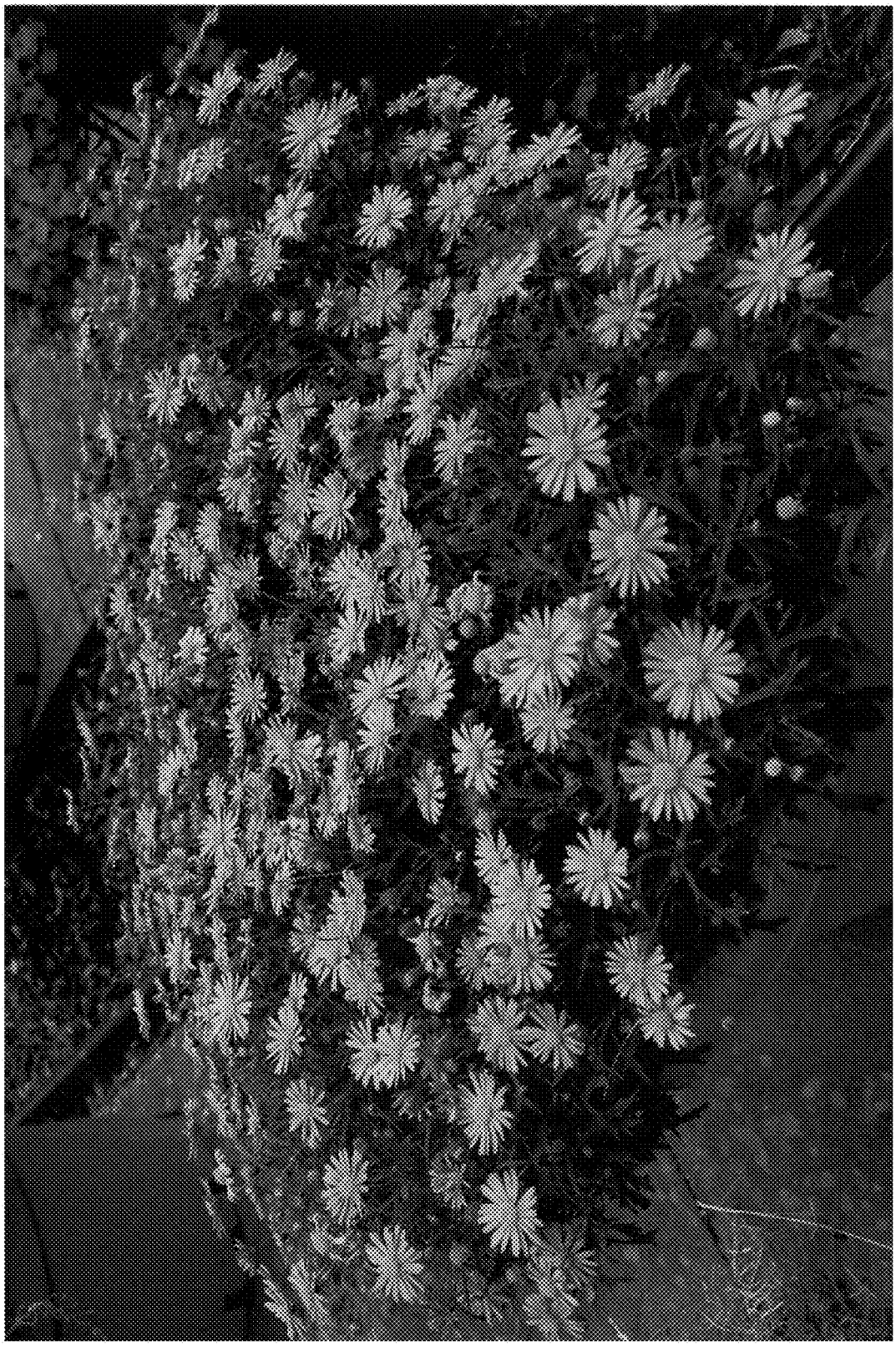

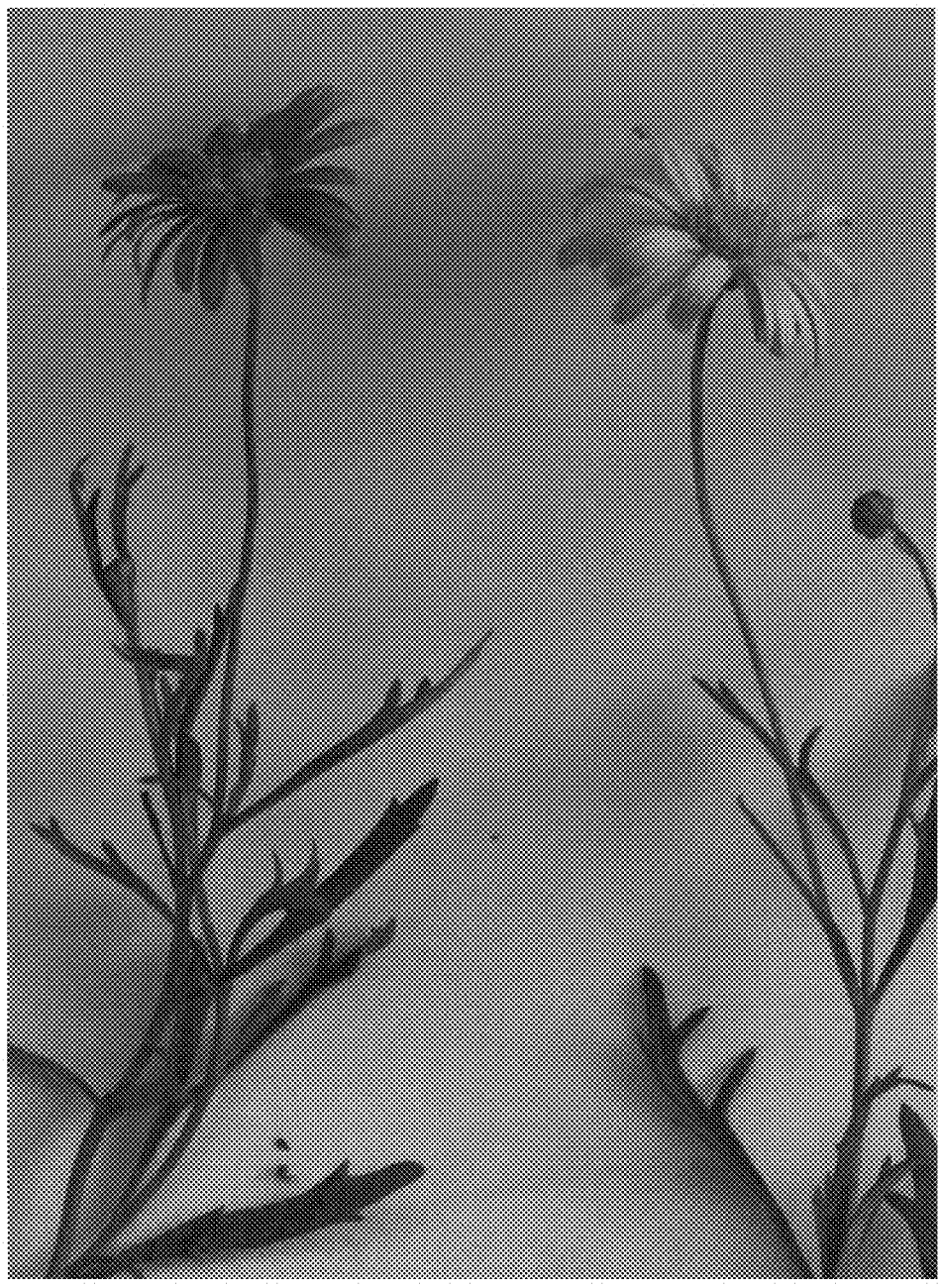

* * * * *